(12) United States Patent
Wang et al.

(10) Patent No.: US 11,378,554 B2
(45) Date of Patent: Jul. 5, 2022

(54) ULTRASOUND TRANSDUCER STRUCTURE, MANUFACTURING METHODS THEREOF, AND ULTRASOUND PROBE

(71) Applicant: GE Precision Healthcare LLC, Milwaukee, WI (US)

(72) Inventors: Yanju Wang, Hartland, WI (US); Stephen Crynock, Fredonia, WI (US); Craig Mirr, Brookfield, WI (US); Jimmie Autrey Beacham, West Allis, WI (US); Mayank Gupta, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 312 days.

(21) Appl. No.: 16/586,788

(22) Filed: Sep. 27, 2019

(65) Prior Publication Data

US 2021/0096108 A1    Apr. 1, 2021

(51) Int. Cl.
*G01N 29/34* (2006.01)
*B06B 1/06* (2006.01)
*B06B 1/02* (2006.01)

(52) U.S. Cl.
CPC ......... *G01N 29/345* (2013.01); *B06B 1/0215* (2013.01); *B06B 1/06* (2013.01); *G01N 29/343* (2013.01)

(58) Field of Classification Search
CPC .. G01N 29/345; G01N 29/343; B06B 1/0215; B06B 1/06
USPC ........................................................ 73/584
See application file for complete search history.

(56) References Cited

U.S. PATENT DOCUMENTS

| 10,370,532 B2* | 8/2019 | Kobayashi | C08L 63/04 |
| 2001/0015592 A1* | 8/2001 | Sliwa, Jr. | B06B 1/0607 |
| | | | 310/321 |
| 2003/0009873 A1* | 1/2003 | Hatangadi | B06B 1/067 |
| | | | 29/594 |

(Continued)

FOREIGN PATENT DOCUMENTS

| JP | 2007202953 A | 8/2007 |
| JP | 2007208896 A | 8/2007 |
| WO | 2017035496 A1 | 3/2017 |

OTHER PUBLICATIONS

Meng, Y. et al., "Laboratory-Scale Reaction Injection Molding of Poly(Caprolactone) Elastomers for Rapid Prototyping of Stimuli-Responsive Thermosets," Rubber Chemistry and Technology, vol. 90, No. 2, Jun. 2017, 11 pages.

*Primary Examiner* — Lisa M Caputo
*Assistant Examiner* — Rose M Miller
(74) *Attorney, Agent, or Firm* — McCoy Russell LLP

(57) ABSTRACT

Various methods and systems are provided for an ultrasound transducer structure for an ultrasound probe and methods of manufacturing thereof. In one example, the ultrasound transducer structure may include a lens, an acoustic stack disposed on the lens, and an acoustic backing material bonded to a side of the acoustic stack facing away from the lens without any intervening layer between the acoustic backing material and the acoustic stack, such that the acoustic backing material is in face-sharing contact with the side of the acoustic stack, wherein the acoustic backing material is composed of a solidified blend comprising a backing polymer.

19 Claims, 7 Drawing Sheets

(56) References Cited

U.S. PATENT DOCUMENTS

| | | | |
|---|---|---|---|
| 2004/0015084 A1* | 1/2004 | Flesch | A61B 8/4483 600/466 |
| 2004/0049900 A1* | 3/2004 | Emery | B06B 1/0629 29/25.35 |
| 2008/0037808 A1* | 2/2008 | Sawada | B06B 1/0622 381/190 |
| 2019/0298306 A1* | 10/2019 | Kondo | A61B 8/4483 |
| 2020/0315577 A1* | 10/2020 | Lee | A61B 8/4494 |

* cited by examiner

ULTRASOUND TRANSDUCER STRUCTURE, MANUFACTURING METHODS THEREOF, AND ULTRASOUND PROBE

FIELD

Embodiments of the subject matter disclosed herein relate to an ultrasound transducer structure for an ultrasound probe and methods of manufacturing thereof.

BACKGROUND

An ultrasound probe may include various components mechanically, conductively, or chemically coupled to form an ultrasound transducer structure within a housing. For example, the ultrasound probe may include an acoustic backing material (also referred to as an acoustic absorber or a carrier) adhered to an acoustic stack. The acoustic stack may be disposed on a lens. Further, the ultrasound probe may be communicatively coupled to a controller of an ultrasound imaging system. In this way, the ultrasound probe may receive and transmit ultrasonic acoustic waves to image a subject, such as a patient.

A method of manufacturing the ultrasound transducer structure may include machining the acoustic backing material, followed by laminating the acoustic backing material to the acoustic stack disposed on the lens. Such manufacturing methods attempt to address strict geometry requirements in aligning a surface of the acoustic stack with a surface of the acoustic backing material in order to achieve sufficient functionality. As recognized by the inventors herein, since the lamination step is often performed by providing a further adhesive layer between the acoustic stack and the acoustic backing material, such strict geometry requirements may be difficult to achieve due to regions of uneven thickness in the adhesive layers, resulting in correspondingly uneven shrinkage ratios and acoustic layer warpage. High temperatures employed to melt the various components forming the acoustic backing material may further exacerbate uneven shrinkage ratios in the ultrasound transducer structure.

BRIEF DESCRIPTION

In one embodiment, an ultrasound transducer structure may include a lens, an acoustic stack disposed on the lens, and an acoustic backing material bonded to a side of the acoustic stack facing away from the lens without any intervening layer between the acoustic backing material and the acoustic stack, such that the acoustic backing material is in face-sharing contact with the side of the acoustic stack, wherein the acoustic backing material is composed of a solidified blend comprising a backing polymer.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
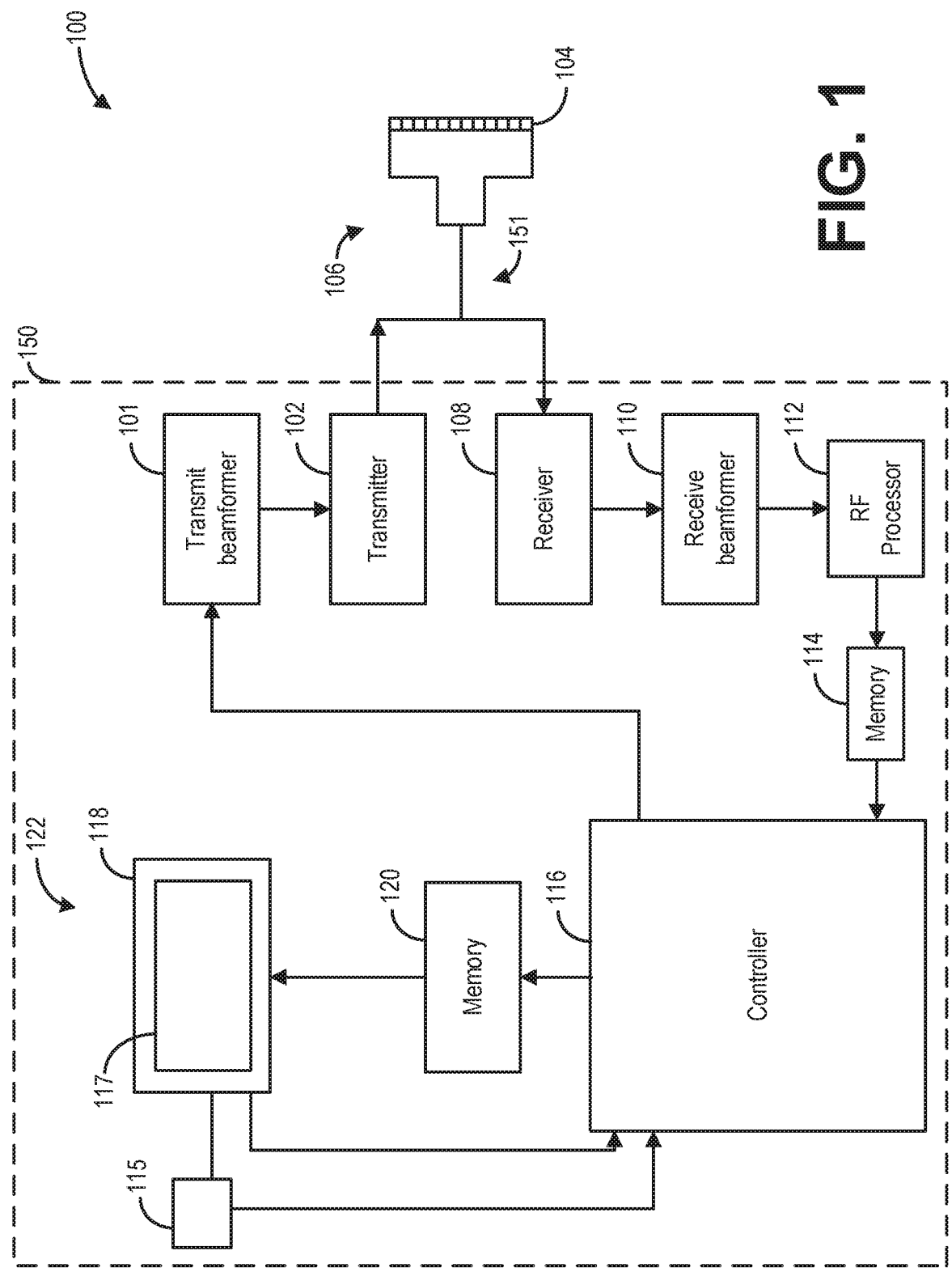
FIG. 1 shows an example ultrasound imaging system according to an exemplary embodiment.
Figure 2:
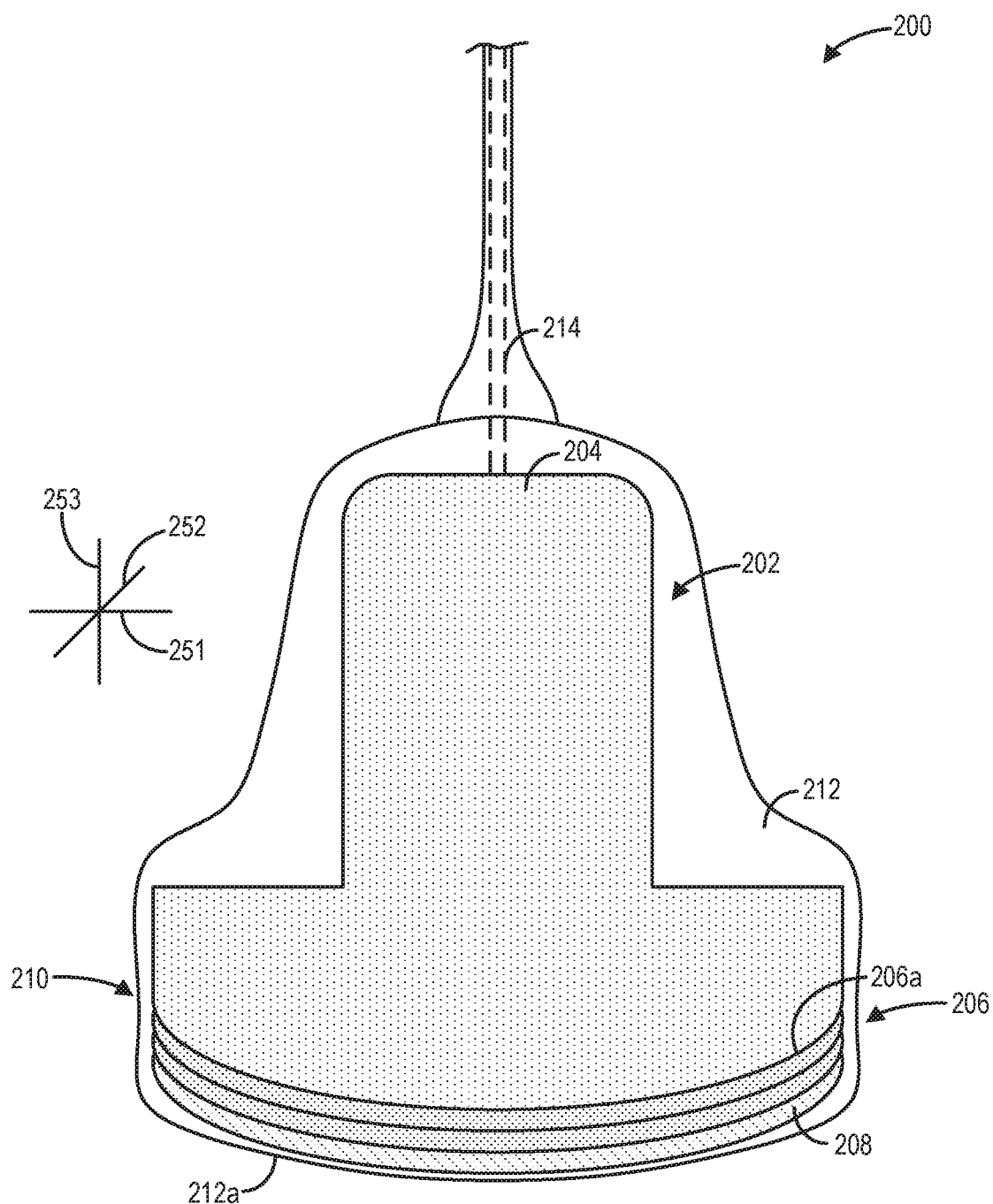
FIG. 2 shows a schematic diagram of an ultrasound probe including an ultrasound transducer structure, according to an embodiment.
Figure 4:
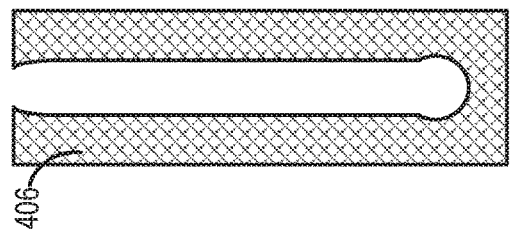
FIG. 4 shows various exemplary mold configurations for manufacturing the ultrasound transducer structure, according to an embodiment.
Figure 4:
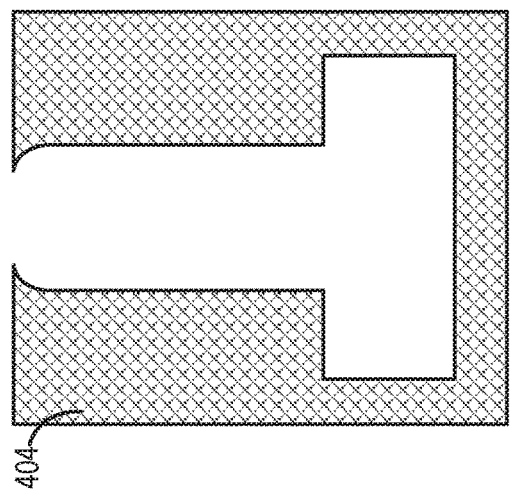
Figure 4:
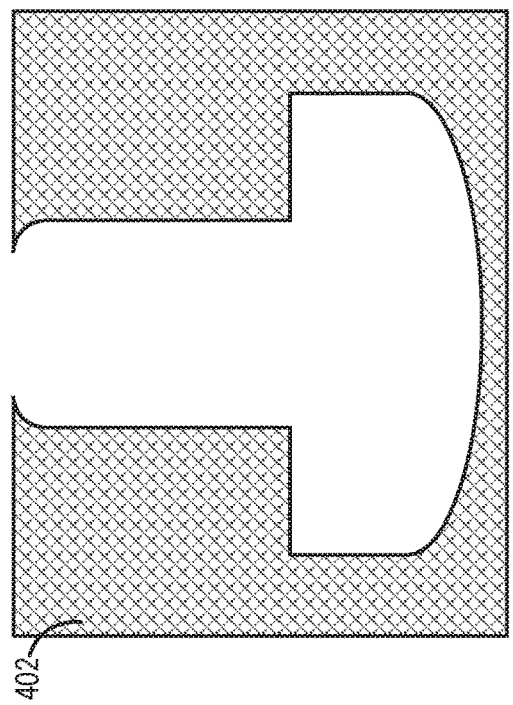
Figure 5:
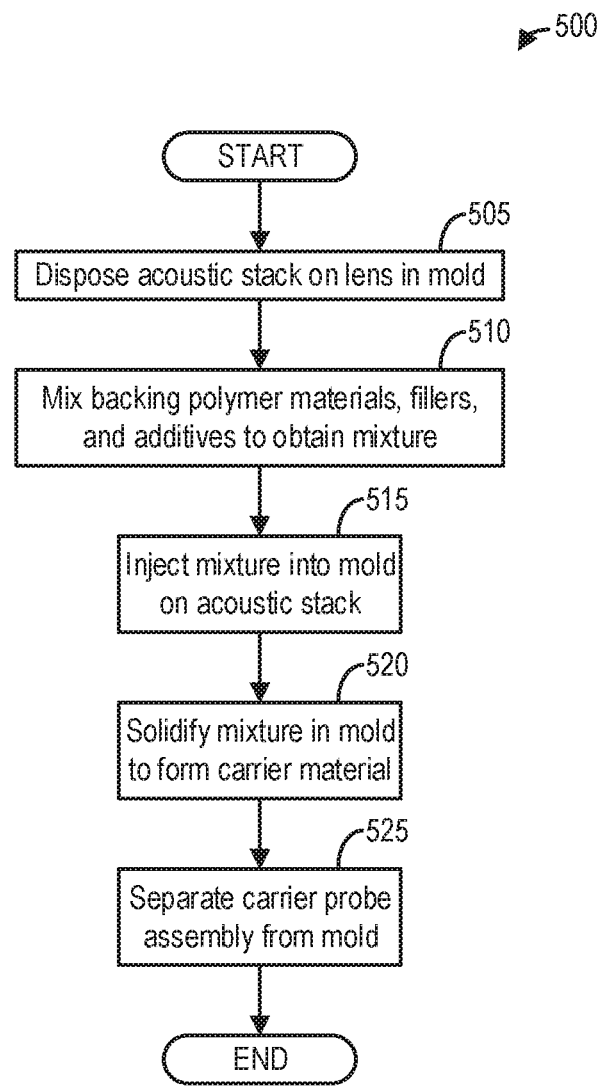
FIG. 5 shows a flow chart of a method for manufacturing the ultrasound transducer structure, according to an embodiment.

The following description relates to various embodiments of an ultrasound probe including an ultrasound transducer structure, and methods of manufacturing the ultrasound transducer structure. One example ultrasound imaging system including the ultrasound probe is depicted in FIG. 1. FIG. 2 depicts an example ultrasound probe including the ultrasound transducer structure. FIGS. 3A-3E schematically illustrate steps of an example manufacturing process for the ultrasound transducer structure, where reactive injection overmolding is employed to bond an acoustic backing material to an acoustic stack absent an adhesive layer. Exemplary mold configurations for the example manufacturing process are depicted at FIG. 4. A corresponding method for manufacturing the ultrasound transducer structure is depicted at FIG. 5.

FIG. 1 depicts a block diagram of a system 100 according to one embodiment. In the illustrated embodiment, the system 100 is an imaging system and, more specifically, an ultrasound imaging system. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric elements including piezoceramics, high-dielectric ceramics, single crystals, etc., within a diagnostic ultrasound probe 106 (or transducer) to emit ultrasonic signals (e.g., continuous or pulsed) into a body or volume (not shown) of a subject. The elements 104 and the probe 106 may have a variety of geometries. The ultrasonic signals are back-scattered from structures in a body, for example, an inserted needle, to produce echoes that return to the elements 104. The echoes are received by a receiver 108. The received echoes are provided to a receive beamformer 110 that performs beamforming and outputs a radio frequency (RF) signal. The RF signal is then provided to an RF processor 112 that processes the RF signal. Alternatively, the RF processor 112 may include a complex demodulator (not shown) that demodulates the RF signal to form I/Q data pairs representative of the echo signals. The RF or I/Q signal data may then be provided directly to a memory 114 for storage (for example, temporary storage). The system 100 also includes a system controller 116 that may be part of a single processing unit (e.g., processor) or distributed across multiple processing units. The system controller 116 is configured to control operation of the system 100.

For example, the system controller 116 may include an image-processing module that receives image data (e.g., ultrasound signals in the form of RF signal data or I/Q data pairs) and processes image data. For example, the image-processing module may process the ultrasound signals to generate two-dimensional (2D) slices or frames of ultrasound information (e.g., ultrasound images) or ultrasound waveforms (e.g., continuous or pulse wave Doppler spectrum or waveforms) for displaying to the operator. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. Further, in some examples, the one or more processing operations may include one or more image transforms, such as a Radon transform for identifying linear features in the ultrasound images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices or waveforms of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, 2D data sets, spectral Doppler data sets, and/or volumetric data sets by various techniques (for example, three-dimensional (3D) scanning, real-time 3D imaging, volume scanning, 2D scanning with probes having positioning sensors, freehand scanning using a voxel correlation technique, scanning using 2D or matrix array probes, and the like). Ultrasound spectrum (e.g., waveforms) and/or images may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In one embodiment, a touchpad may be configured to the system controller 116 and display area 117, such that when a user moves a finger/glove/stylus across the face of the touchpad, a cursor atop the ultrasound image or Doppler spectrum on the display device 118 moves in a corresponding manner.

In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator (such as a request to adjust or update an orientation of a displayed image). The display device 118 also communicates information from the controller 116 to the operator by displaying the information to the operator. The display device 118 and/or the user interface 122 may also communicate audibly. The display device 118 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

In addition to the image-processing module, the system controller 116 may also include one or more of a graphics module, an initialization module, a tracking module, and an analysis module. The image-processing module, the graphics module, the initialization module, the tracking module, and/or the analysis module may coordinate with one another to present information to the operator during and/or after the imaging session. For example, the image-processing module may be configured to display an acquired image on the display device 118, and the graphics module may be configured to display designated graphics along with the displayed image, such as selectable icons (e.g., image rotation icons) and measurement parameters (e.g., data) relating to the image.

The screen of a display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity (e.g., blood flow velocity), color flow velocity, texture, graininess, contractility, deformation, and rate of deformation value. The series of pixels then make up the displayed image and/or Doppler spectrum generated from the acquired ultrasound data.

In some examples, an ultrasound console 150 may house the RF processor 112, the memory 114, the one or more user interface input devices 115, the system controller 116, the image memory 120, and the user interface 122 (including the display device 118 with the display area 117). The ultrasound console 150 may further house the transmit beamformer 101, the transmitter 102, the receiver 108, and the receive beamformer 110. Further, in some examples, a cable 151 may communicatively couple the probe 106 to the console 150, such that received ultrasound data may be transmitted from the probe 106 to the console 150 via the cable 151. In other embodiments not depicted at FIG. 1, the probe 106 may be communicatively coupled to the console 150 via one or more wireless networks. Thus, transmission of data and signals between the probe 106 and the console 150 for generating and interpreting ultrasound images may be enabled via the cable 151 or the one or more wireless networks.

Referring now to FIG. 2, an ultrasound probe 200 including an ultrasound transducer structure 202 (also referred to as an ultrasound transducer assembly) is schematically depicted according to one embodiment. In one example, the ultrasound probe 200 is the ultrasound probe 106 shown in FIG. 1. The ultrasound probe 200 may further include a housing 212 inside of which the ultrasound transducer structure 202 is positioned. The housing 212 may be configured such that the housing 212 approximately conforms to a shape of the ultrasound transducer structure 202. In some embodiments, the ultrasound probe 200 may further include a cable 214 conductively coupled to the ultrasound transducer structure 202 and extending outward from the ultrasound transducer structure 202, such that the cable 214 may be partially enclosed in the housing 212. In one examples, the cable 214 is the cable 151 shown in FIG. 1. As such, the ultrasound probe 200 may be communicatively coupled to an ultrasound console (e.g., 150) via the cable 214. In other embodiments not depicted at FIG. 2, the ultrasound probe 200 may be communicatively coupled to the ultrasound console via one or more wireless networks. Mutually perpendicular axes 251, 252, and 253 are depicted at FIG. 2 for indicating relative positioning of components of the ultrasound probe 200 with respect to one another.

For example, the ultrasound transducer structure 202 may include an acoustic backing material 204, an acoustic stack 206, and a lens 208 aligned along the axis 253 within a tolerance of less than 25 µm. In some examples, the tolerance may be less than 20 µm. In some examples, the tolerance may be less than 15 µm. In some examples, the tolerance may be less than 10 µm. In some examples, the tolerance may be less than 5 µm. The lens 208 may be positioned at a peripheral portion 212a of the housing 212 through which ultrasound radiation may be transmitted and received. The acoustic stack 206 may be conductively coupled to the lens 208, positioned along the axis 253 so as to not obstruct receipt of ultrasonic waves by the lens 208. The acoustic stack 206 may include an array of piezoelectric elements, for example, for converting received ultrasound vibrations into voltage signals and for converting received voltage signals into ultrasound vibrations. The acoustic backing material 204 may then be bonded without adhesives to a side 206a of the acoustic stack 206 facing away from the lens 208. As used herein, "adhesive" may refer to a composition employed with a sole intended function of adhering one component of an ultrasound transducer structure to another component thereof, such that the components may be bound together by a presence of the adhesive. For example, adhesives may include any glues, cements, mucilages, pastes, etc. employed to adhere two components of an ultrasound transducer structure together, such as an acoustic backing material and an acoustic stack. As specific examples, adhesives may include EPO-TEK® 330 or DP460EG.

Various configurations may be employed for the acoustic backing material 204 within the scope of the present disclosure. In the depicted embodiment, a portion of the acoustic backing material 204 adjacent to the acoustic stack 206 may be wider along the axis 251 than a portion of the acoustic backing material 204 adjacent to the cable 214. A depth of the acoustic backing material 204 along the axis 252 is not particularly limited, but may be such that the ultrasound transducer structure 202 positioned within the housing 212 is comfortably held by a hand. The acoustic backing material 204 may include various components with acoustic-dampening properties, such that ultrasonic waves generated by the acoustic stack 206 may largely be prevented from being reflected back to the acoustic stack 206. For example, the acoustic backing material 204 may be composed of a solidified blend of a backing polymer matrix, filler particles, and one or more additives (e.g., hardeners, crosslinkers), where the backing polymer matrix may be formed from a thermoplastic, thermosetting polymer precursors, or a resin, which may be selected in part for the acoustic-dampening properties thereof.

Manufacturing processes for conventional carrier probe assemblies typically involve several steps through which a quality of a produced ultrasound transducer structure may be diminished through aggregated human, random, or machine error. First, acoustic backing materials with desired acoustic properties may be selected and purchased as allowed based upon commercial availability. Then, the acoustic backing materials may be molded or machined into a desired geometry or configuration. Finally, the acoustic backing materials may be laminated to an acoustic stack via an adhesive after screening the adhesive and optimizing lamination process parameters for adhesive layer thickness control, curing conditions, lamination pressure, etc.

Conventional acoustic backing materials may include aluminum or high-melting point thermoplastic polymers mixed with various fillers. However, some conventional acoustic backing materials (e.g., aluminum) may have acoustic-reflective properties. As such, some conventional carrier probe assemblies may include further layers to provide acoustic cancellation so as to prevent echoes from reaching the acoustic stack. Further, a geometry tolerance on a surface of the acoustic backing material is necessarily strict enough to allow the surface of the acoustic backing material to align with a corresponding surface of the acoustic stack. For example, this geometry tolerance may necessarily be on the order of a few microns. Conventional thermomolding processes may be unable to satisfy the strict geometry tolerance absent further machining (e.g., polishing), particularly when a configuration of the acoustic backing material has varying thicknesses at different locations, resulting in correspondingly varying shrinkage ratios. Due to the strict geometry tolerance, the lamination of the acoustic backing material to the acoustic stack may be particularly involved. Numerous manual steps, each a potential source of error, are involved in conventional lamination processes, such as taping, applying the adhesive, alignment of components, curing the adhesive, etc. As a result, a manufacturing scrap rate for conventional carrier probe assemblies may be undesirably high.

According to embodiments disclosed herein, the above-described issues may be at least partly addressed by manufacturing the acoustic backing material 204 with a reactive injection overmolding process. During manufacture, a mixture of backing polymer materials, fillers, and additives may be injected into a mold with the acoustic stack 206 and the lens 208 pre-assembled therein. The acoustic backing material 204 may then be formed and directly attached to the side 206a of the acoustic stack 206 through curing or solidifying the mixture at room temperature or a slightly elevated temperature (e.g., less than 200° C.), such that no adhesives may be disposed in an interface region 210 between the acoustic backing material 204 and the acoustic stack 206. In some embodiments, no adhesive layers may be disposed in the interface region 210 between the acoustic backing material 204 and the acoustic stack 206. In this way, the acoustic backing material 204 may be in face-sharing contact (e.g., in direct contact at a continuous interface) with the acoustic stack 210 without any intervening layers of adhesive or any other material. In some embodiments, no adhesives may be disposed on external surfaces or at interfaces of the acoustic backing material 204 and the acoustic stack 210. In some embodiments, no adhesives or adhesive layers may be disposed at an interface between any two of the depicted components of the ultrasound transducer structure 202. In some embodiments, the ultrasound transducer structure 202 may include no adhesives or adhesive layers.

In this way, the ultrasound transducer structure 202 may be manufactured having desired and tuned acoustic properties, such as acoustic impedance and attenuation, with minimal restrictions on overall probe design. As such, the various components included in the acoustic backing material 204 may act in tandem to provide acoustic interference patterns and therefore attenuate received acoustic energy. For example, the backing polymer matrix (a relatively low density material) and the filler particles (a relatively high density material) may act in tandem to respectively increase acoustic absorption and acoustic reflectivity. Further, such acoustic reflectivity may aid in phase or amplitude manipulation.

Specifically, employing reactive injection overmolding combines machining and lamination steps into a single process, providing several distinct advantages. As a first example, the strict geometry tolerance necessary to match the acoustic backing material 204 to the acoustic stack 206 may be inherently achieved via a liquid mixture of raw materials, such as resins, other polymer precursors, fillers, and additives contacting the acoustic stack 206 directly during manufacturing, such that a geometry of an interface between the acoustic backing material 204 and the acoustic stack 206 may be determined based on a shape of the acoustic stack 206 alone. As a second example, as opposed to the high melting temperature required by conventional ultrasound transducer structure manufacturing processes, the reactive injection overmolding process may employ curing or solidifying at comparatively lower temperatures, thus reducing shrinkage ratio differences due to different thicknesses arising from heat-induced warping that amplify manufacturing imperfections. As a third example, since a location of the acoustic stack 206 in the mold and a configuration of the acoustic backing material 204 may be fixed by judicious mold design, no extra alignment step is necessary. As a fourth example, extra adhesive layers between the acoustic backing material 204 and the acoustic stack 206 may be eliminated. In turn, such adhesive layer elimination simplifies the overall manufacturing process by obviating selection of adhesives to achieve a desired thickness of the overall ultrasound transducer structure and acoustic stack warpage due to thermal mismatch between the adhesive and the acoustic stack, thereby improving upon the manufacturing scrap rate. That is, the reactive injection overmolding process may allow for backing polymer materials and additives (e.g., hardeners, crosslinkers) to be pre-mixed and cast directly onto the acoustic stack 206, such that the acoustic backing material 204 may be directly attached to the acoustic stack 206 with stronger bonding following curing or solidification. Because the adhesive provides two interfaces (e.g., between the acoustic backing material 204 and the adhesive, and between the acoustic stack 206 and the adhesive) and the reactive injection overmolding process provides only one interface (e.g., between the acoustic backing material 204 and the acoustic stack 206), there are fewer possible locations of structural failure when the reactive injection overmolding process is employed in place of the adhesive, thereby improving bonding between the acoustic backing material 204 and the acoustic stack 206.

Thus, manufacturing the ultrasound transducer structure 202 via reactive injection overmolding simplifies production, at least by reducing alignment steps, eliminating adhesive layers between the acoustic backing material 204 and the acoustic stack 206, and providing a stronger bonding interface between the acoustic backing material 204 and the acoustic stack 206. Further, since reactive injection overmolding may utilize mixtures of raw materials, greater flexibility may be provided in selecting a composition of the acoustic backing material 204, as many of these raw materials may be combined to achieve the desired acoustic properties. Additionally, the backing polymer materials may be integrated throughout the acoustic backing material 204, as opposed to forming independent layers which may require further lamination steps. In this way, embodiments of the ultrasound transducer structure provided by the present disclosure may be manufactured with minimal or no adhesives, laminations, and alignments, thus resulting in higher reproducibility, faster manufacturing speeds, and lower costs.

Referring now to FIGS. 3A-3E, schematic steps 300, 320, 340, 360, and 380 illustrating an example manufacturing process of the ultrasound transducer structure 202 are depicted according to one embodiment. The ultrasound transducer structure 202 may be included in an ultrasound probe, such as the ultrasound probes described above with reference to FIGS. 1 and 2, which may be communicatively coupled to an ultrasound console, such as the ultrasound console 150 described above with reference to FIG. 1. A reactive injection overmolding process may be employed to manufacture the ultrasound transducer structure 202, which may provide stronger bonding between the acoustic backing material 204 and the acoustic stack 206 included therein, and may simplify the example manufacturing process as a whole by combining machining the acoustic backing material 204 and subsequent lamination of the acoustic backing material 204 to the acoustic stack 206 into one process.

Figure 3A:
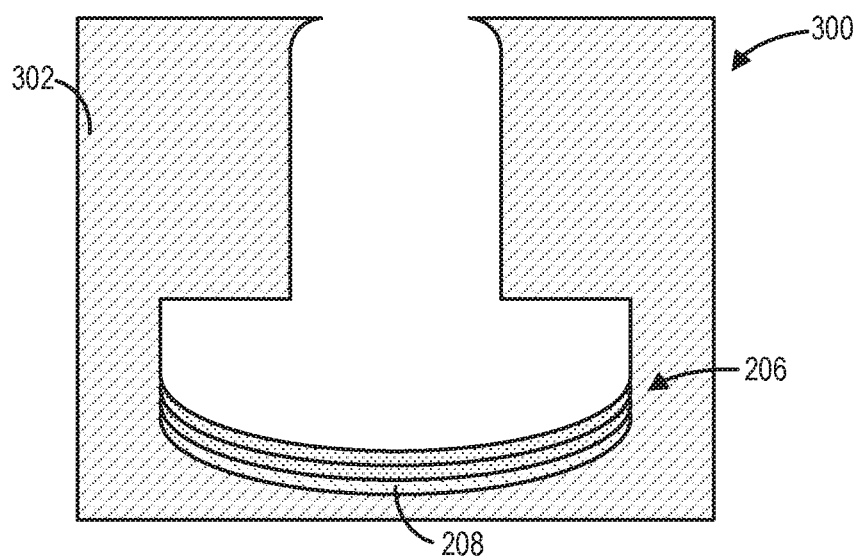
FIGS. 3A-3E shows schematic diagrams illustrating an example manufacturing process of the ultrasound transducer structure, according to an embodiment.

Referring now to FIG. 3A, at first schematic step 300, the lens 208 may be disposed in a mold 302, and the acoustic stack 206 may further be disposed on the lens 208. The mold 302 may be machined or additive printed from various plastics or metals. In some embodiments, the mold 302 may be composed of polymers chemically or thermally compatible with materials employed for the various components of the ultrasound transducer structure 202 and the reactive injection overmolding process. Additionally, the mold 302 may be manufactured from a single material, a plurality of materials, or from a material coated with a releasing or sacrificing layer. The releasing or sacrificing layer may be coated using any coating methods known in the art, such as thin film coating processes or additive printing. Further, the releasing or sacrificing layer may be composed of mold-releasing spray chemicals or polymers which may be peeled off or dissolved by organic or aqueous solvents to facilitate demolding. Numerous configurations may be hollowed out within the mold 302 depending on a desired configuration of the acoustic backing material 204 and shapes of the lens 208 and the acoustic stack 206. Various exemplary mold configurations are discussed below with reference to FIG. 4, though it will be appreciated that numerous other mold configurations may be employed within the scope of the present disclosure.

Figure 3B:
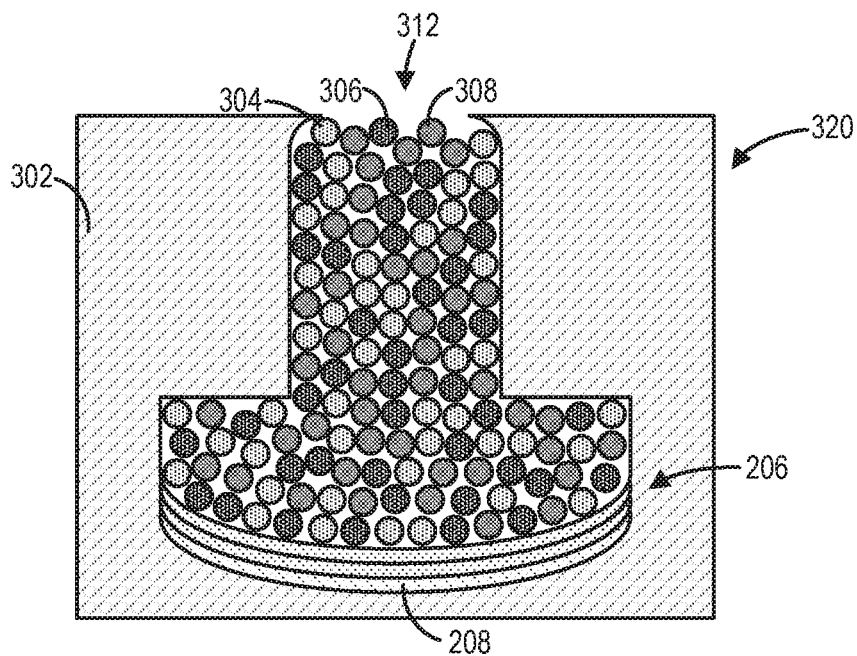

Referring now to FIG. 3B, at second schematic step 320, a liquid or semisolid mixture 312 (e.g., a slurry, dispersion, suspension, paste, solution, etc.) may be injected into the mold 302 under pressure or in a vacuum, where the mixture 312 may include a homogeneous distribution of one or more backing polymer precursors 304, fillers 306, and additives 308. In some examples, the one or more backing polymer precursors 304 may include one or more of thermoplastics, thermosetting polymer precursors, and resins. In some examples, the thermoplastics may include one or more of polypropylene, polystyrene, poly(methyl methacrylate), polycarbonate, polyurethane, etc. In some examples, the thermosetting polymer precursors may include one or more epoxies, such as bisphenol-based epoxies (e.g., EPO-TEK® 301, Loctite®), and cationic, anionic, room-temperature, or heat-curing crosslinkers. As such, the one or more backing polymer precursors 304 may be selected to form, upon curing or solidification, backing polymers which may possess sufficient strength to hold other components of the mixture 312 in place and outlast a service lifetime for the ultrasound transducer structure 202. In embodiments wherein the one or more backing polymer precursors 304 include thermosetting polymer precursors, the backing polymer may include one or more thermosetting polymers formed from at least two of the thermosetting polymer precursors upon curing or solidification. The one or more thermosetting polymers may include one or more of epoxies, polyurethanes, phenol formaldehyde resins, melamine resins, polyacrylates, polyimides, silicones (e.g., RTV 630), silicon hybrid epoxies (e.g., Gelest 1092), and the like.

The one or more fillers 306 may include additional polymers, metals, organic materials, or inorganic materials. In some examples, the one or more fillers 306 may include metal or inorganic particles which meet desired acoustic properties. For example, the one or more fillers 306 may include one or more of tungsten, stainless steel, silver, silica, oxides, and organic salts. In some examples, the one or more fillers 306 may be selected to provide high heat conductivity and thereby function to diffuse heat during fabrication or use of the ultrasound probe. As such, in some embodiments, no further heat shields or heat spreaders may be included in the mixture 312 or in the final ultrasound transducer structure 202. In some examples, the one or more additives 308 may include one or more of hardeners, crosslinkers, surfactants, polymerization initiators, polymerization accelerators, and stabilizers. Thus, in some embodiments, at least some of the one or more additives 308 may react with the one or more backing polymer precursors 304 to form the one or more backing polymers.

Figure 3C:
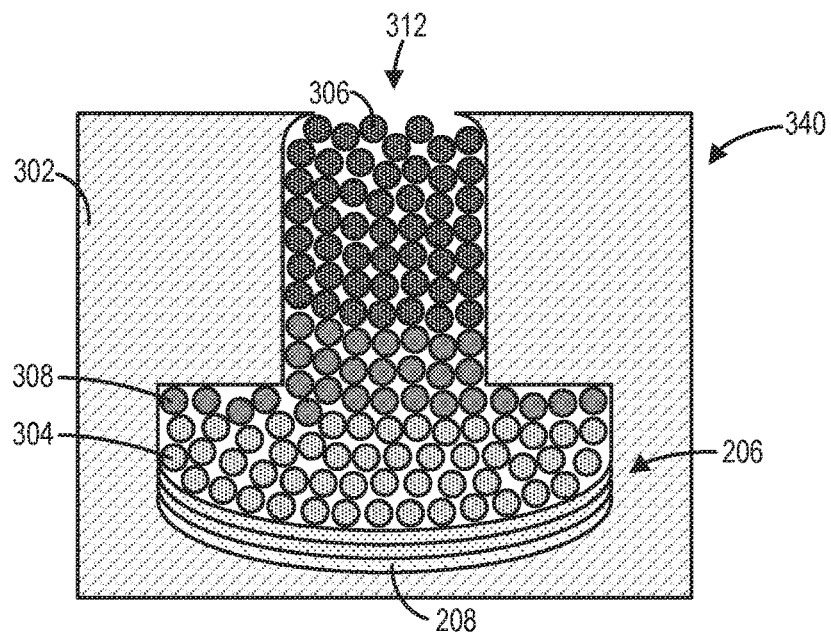

Referring now to FIG. 3C, at third schematic step 340, a liquid or semisolid mixture 312 (e.g., a slurry, dispersion, suspension, paste, solution, etc.) may be injected into the mold 302 under pressure or in a vacuum, where the mixture 312 may include a uniform density gradient of one or more backing polymer precursors 304, fillers 306, and additives 308. It will be appreciated that third schematic step 340 may be an alternative to second schematic step 320, differing only in a distribution of components of the mixture 312.

In some embodiments, such as in the specific embodiment depicted in FIG. 3C, the uniform density gradient may be formed by injecting the various components of the mixture 312 in sequence, such that an approximately layered configuration of the components of the mixture 312 may be achieved. In some embodiments, the uniform density gradient may include each component of the mixture 312 in any given region, but in differing proportions. For example, a higher density region may have a higher proportion by weight of the one or more fillers 306, whereas a lower density region may have a higher proportion by weight of the one or more backing polymer precursors 304. Upon solidification, adhesion at interfaces between higher and lower density regions may increase, such that the formed acoustic backing material 204 may retain structural integrity. In some embodiments, various geometrical regions may be formed having differing compositions, such as via ultrasonic, magnetic, or electrical means. In this way, an acoustic wavefront may be manipulated by employing relative configurations of the various components of the mixture 312 to adjust a phase or amplitude of the acoustic wavefront via linear modulation (e.g., acoustic refraction), periodic modulation (e.g., acoustic grating), and/or quadratic modulation (e.g., acoustic lensing or via a graded-index waveguide).

Figure 3D:
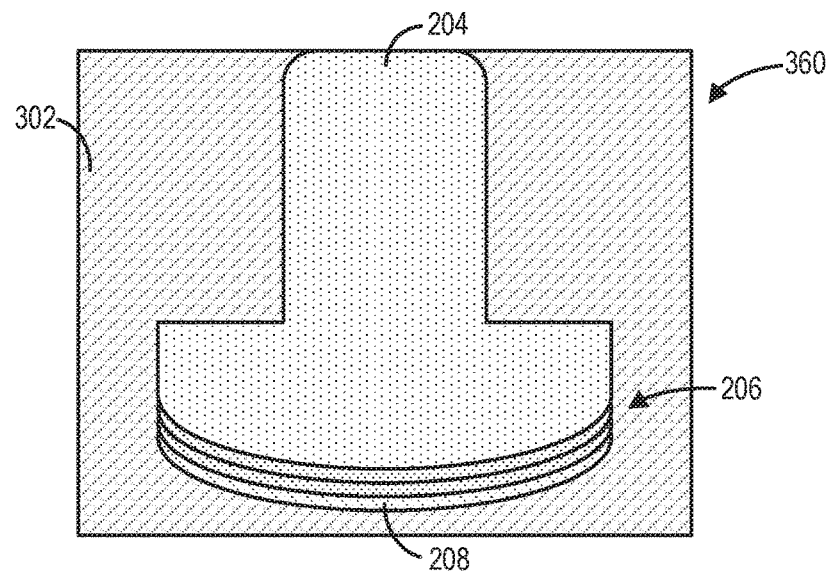

Referring now to FIG. 3D, at fourth schematic step 360, the mixture 312 may be cured or solidified to form the acoustic backing material 204. As such, the acoustic backing material 204 may be considered a solidified polymer composite blend of one or more backing polymers (e.g., formed from the one or more backing polymer precursors 304), fillers 306, and additives 308. The curing or solidification of the mixture 312 may be performed at room temperature or at slightly elevated temperatures (e.g., less than 200° C.). In this way, the reactive injection overmolding process may not employ the higher temperatures used in conventional ultrasound transducer structure manufacturing processes to melt one or more backing materials. As a result, compositional requirements for the mold 302 may be less restrictive in that a wider and more flexible range of materials may be used to form the mold 302, which may allow for further lower overall costs.

The one or more backing polymer precursors 304 and the fillers 306 may be selected so as to provide a composition which, upon curing or solidification to form the solidified blend, satisfies the desired acoustic properties for a given ultrasound probe. Acoustic advantages may be obtained based on interfacial interactions (e.g., adhesion) between the one or more backing polymers (e.g., formed from the one or more backing polymer precursors 304) and the fillers 306, filler composition, filler particle size, and an overall distribution of the fillers 306 in the one or more backing polymers. For example, the one or more backing polymers may constitute relatively softer materials surrounding relatively harder filler particles (e.g., 306). In this way, the solidified blend may confer acoustic-cancelling properties to the acoustic backing material, where the harder filler particles reflect acoustics which may be counterbalanced by an acoustic-dampening effect provided by the softer materials.

Figure 3E:
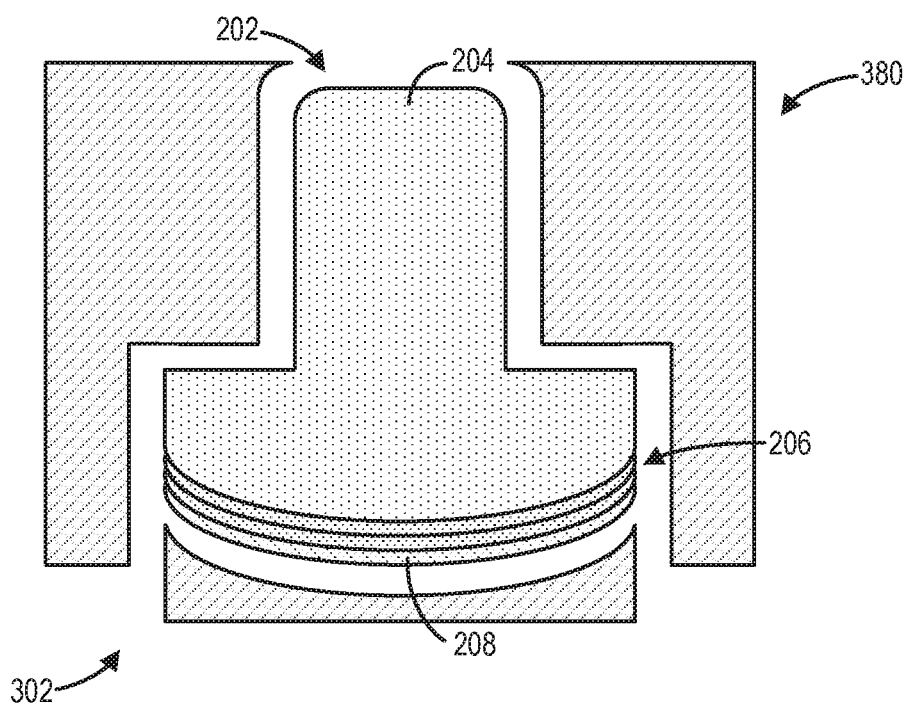

Referring now to FIG. 3E, at fifth schematic step 380, the mold 302 may be demolded in one or more pieces to obtain the ultrasound transducer structure 202. After demolding the mold 302, the acoustic stack 206 may bond to the acoustic backing material 204 without an adhesive layer. In some embodiments, a bonding between the adhesive stack 206 and the acoustic backing material 204 may be stronger than a bonding provided by the adhesive layer. Further, by using the mold 302 and relative low temperatures to form the ultrasound transducer structure 202, an alignment of the acoustic backing material 204, the acoustic stack 206, and the lens 208 may be controlled to a strict geometry tolerance. In this way, the ultrasound transducer structure 202 formed via the reactive injection overmolding process may have desirable acoustic properties, eliminate excess adhesive, and require no further machining or polishing to meet geometry tolerances.

Referring now to FIG. 4, three exemplary mold configurations 402, 404, and 406 for manufacturing an ultrasound transducer structure are depicted. In one example, the ultrasound transducer structure may be the ultrasound transducer structure 202 described above with reference to FIG. 2. Each of the mold configurations 402, 404, and 406 may be considered as one embodiment of the mold 302 described above with reference to FIGS. 3A-3E, and may be employed to manufacture a specific configuration of the ultrasound transducer structure for a specific purpose. As a first example, the mold configuration 402 may be used to manufacture an ultrasound transducer structure having a curved lens, which may aid in increasing a field of view for imaging larger organs or regions in a subject, such as a medical patient. As such, the ultrasound transducer structure manufactured with the mold configuration 402 may be incorporated in a convex ultrasound probe, for example. As a second example, the mold configuration 404 may be used to manufacture an ultrasound transducer structure having a square lens, which may be used for high-resolution or near-surface imaging, or for small footprint applications, such as for cardiac imaging. As such, the ultrasound transducer structure manufactured with the mold configuration 404 may be incorporated in a linear or a sector ultrasound probe, for example. As a third example, the mold configuration 406 may be used to manufacture an ultrasound transducer structure having a long, slender tip, which may facilitate insertion into body openings or cavities such as for imaging an esophagus. As such, the ultrasound transducer structure manufactured with the mold configuration 406 may be incorporated in an endocavitary ultrasound probe, such as an endovaginal or an endorectal ultrasound probe, for example.

It will be appreciated that many further mold configurations may be included within the scope of this disclosure, and that the exemplary mold configurations depicted at FIG. 4 should not be understood as limiting the embodiments described herein. For example, a mold may be configured for fabrication of an ultrasound transducer structure to be included in any type of ultrasound probe (e.g., linear probes, curved or convex probes, sector probes, or endocavitary probes of any configuration). In this way, a mold configuration may be selected to fabricate an ultrasound transducer structure for a desired ultrasound probe configuration, and thus the manufacturing process of the present disclosure may be extensible to a wide variety of ultrasound imaging applications.

Referring now to FIG. 5, a flow chart of a method 500 for manufacturing an ultrasound transducer structure using a reactive injection overmolding process is depicted, according to one embodiment. Method 500 is described below with regard to the embodiments depicted in FIGS. 1-3D, though it should be appreciated that method 500 may be implemented to manufacture other embodiments without departing from the scope of the present disclosure. As one example, method 500 may be employed to manufacture the ultrasound transducer structure 202 of FIG. 2.

Method 500 may begin at 505, where an acoustic stack (e.g., 206) may be disposed on a lens (e.g., 208) in a cavity of a mold (e.g., 302). In some embodiments, each of the acoustic stack and the lens may be pre-assembled in the cavity of the mold upon fabrication of the mold. Further, an exemplary embodiment of 505 is depicted as first schematic step 300, as described above with reference to FIG. 3A. In this way, the mold may be configured specifically for a given acoustic stack and lens.

At 510, method 500 may include mixing one or more backing polymer materials (e.g., 304), one or more fillers (e.g., 306), and one or more additives (e.g., 308) to obtain a mixture (e.g., 312). In some embodiments, the one or more backing polymer materials include one or more or a combination of thermoplastics, thermosetting polymer precursors, and resins. In some embodiments, the one or more fillers may include one or more or a combination of metal particles and other inorganic particles. In some embodiments, the one or more additives may include one or more or a combination of hardeners, crosslinkers, surfactants, polymerization initiators, polymerization accelerators, and stabilizers. In some embodiments, the mixture may be a homogeneous distribution of the one or more backing materials, the one or more fillers, and the one or more additives. In some embodiments, the mixture may be a uniform density gradient of the one or more backing materials, the one or more fillers, and the one or more additives. In this way, components of the mixture may be selected to tune desired acoustic properties of the finally formed ultrasound transducer structure, thus providing greater flexibility in design over conventional carrier probe assemblies.

At 515, method 500 may include injecting the mixture (e.g., 312) into the cavity of the mold (e.g., 302) such that the mixture contacts a side (e.g., 206*a*) of the acoustic stack (e.g., 206) facing away from the lens (e.g., 208). As such, in some examples, the mixture may fill all volume of the cavity of the mold not occupied by the acoustic stack and the lens. Further, exemplary embodiments of 515 are depicted as second schematic step 320, as described above with reference to FIG. 3B, or as third schematic step 340, as described above with reference to FIG. 3C. In this way, the mold may align the acoustic stack, the lens, and an acoustic backing material formed from the mixture in the finally formed ultrasound transducer structure.

At 520, method 500 may include solidifying the mixture (e.g., 312) to form an acoustic backing material (e.g., 204) bonded to the acoustic stack (e.g., 206) without adhesives. Solidifying the mixture may include one or more of curing the mixture (e.g., solidifying the mixture at room temperature) and heating the mixture. In examples wherein solidifying the mixture includes heating the mixture, the heating may be performed at a relatively low temperature, such as 200° C. or less. Solidifying the mixture may further employ thermosetting properties of the one or more backing polymer materials. As an examples, when the one or more backing polymer materials include the one or more thermosetting polymer precursors, a thermosetting polymer may be formed from the thermosetting polymer precursors upon solidification of the mixture. Further, an exemplary embodiment of 520 is depicted as fourth schematic step 360, as described above with reference to FIG. 3D. In this way, manufacturing of the ultrasound transducer structure may be performed without elevated temperatures, thereby controlling for excessive variation in shrinkage ratios of the various components therein.

At 525, method 500 may include separating the ultrasound transducer structure (e.g., 202) from the mold (e.g., 302). By employing the reactive injection overmolding process of the present disclosure, the ultrasound transducer structure may thus be manufactured without an adhesive layer disposed between the acoustic stack (e.g., 206) and the acoustic backing material (e.g., 204). Further, an exemplary embodiment of 525 is depicted as fifth schematic step 380, as described above with reference to FIG. 3E. In this way, the manufacturing process of the ultrasound transducer structure may be simpler, more flexible, and cheaper than manufacturing processes of conventional carrier probe assemblies. Method 500 may then end.

In this way, an ultrasound transducer structure may be manufactured for use in an ultrasound probe of an ultrasound imaging system. The manufacturing may be accomplished via a reactive injection overmolding process, whereby an acoustic backing material is bonded to an acoustic stack by solidifying a mixture of backing polymer materials, fillers, and additives disposed on the acoustic stack. A technical effect of utilizing the reactive injection overmolding process is that no adhesive layer is required for bonding the acoustic backing material to the acoustic stack. As such, more rigid geometry tolerances (e.g., <25 µm) may be met, as issues related to warpage of the adhesive layer may be eliminated. Further, higher temperatures typically employed to melt components of the acoustic backing material may be obviated by using the reactive injection overmolding process, which may be conducted near or at room temperature. A technical effect of such lowered temperatures is that shrinkage ratios of various components of the ultrasound transducer structure may be controlled to within preset geometry tolerances.

In one embodiment, an ultrasound transducer structure comprises a lens, an acoustic stack disposed on the lens, and an acoustic backing material bonded to a side of the acoustic stack facing away from the lens, the acoustic backing material composed of a solidified blend comprising a backing polymer, wherein the ultrasound transducer structure includes no adhesive layer disposed between the acoustic stack and the acoustic backing material. In a first example of the ultrasound transducer structure, the backing polymer is formed from one or more or a combination of thermoplastics, thermosetting polymer precursors, and resins. In a second example of the ultrasound transducer structure, optionally including the first example, no adhesives are disposed on external surfaces or at interfaces of the acoustic backing material and the acoustic stack. In a third example of the ultrasound transducer structure, optionally including one or more of the first and second examples, each of the acoustic backing material, the acoustic stack, and the lens are aligned along an axis within a tolerance of less than 25 µm. In a fourth example of the ultrasound transducer structure, optionally including one or more of the first through third examples, the solidified blend further comprises one or more fillers, the one or more fillers including additional polymers, metals, organic materials, or inorganic materials. In a fifth example of the ultrasound transducer structure, optionally including one or more of the first through fourth examples, the one or more fillers are in a particulate form. In a sixth example of the ultrasound transducer structure, optionally including one or more of the first through fifth examples, the solidified blend further comprises one or more additives including hardeners, crosslinkers, surfactants, polymerization initiators, polymerization accelerators, and stabilizers. In a seventh example of the ultrasound transducer structure, optionally including one or more of the first through sixth examples, a bonding between the adhesive stack and the acoustic backing material is stronger than a bonding provided by the adhesive layer.

In another embodiment, an ultrasound probe comprises a housing, and an ultrasound transducer structure positioned inside the housing, the ultrasound transducer structure comprising a lens, an acoustic stack conductively coupled to the lens, the acoustic stack comprising an array of piezoelectric elements, where the array of piezoelectric elements comprises piezoceramics, high-dielectric ceramics, or single crystals, and an acoustic backing material bonded to a side of the acoustic stack facing away from the lens, the acoustic backing material composed of a solidified blend of a backing polymer matrix, filler particles, and one or more stabilizers, wherein the ultrasound transducer structure includes no adhesives disposed between the acoustic stack and the acoustic backing material, the backing polymer matrix is formed from a thermoplastic, thermosetting polymer precursors, or a resin, and the lens is positioned at a peripheral portion of the housing through which ultrasound radiation is transmitted and received. In a first example of the ultrasound probe, the ultrasound probe further comprises a cable conductively coupled to the ultrasound transducer structure, the cable partially enclosed in the housing, wherein the ultrasound probe is communicatively coupled to an ultrasound console via the cable. In a second example of the ultrasound probe, optionally including the first example, the ultrasound probe is communicatively coupled to an ultrasound console via a wireless network. In a third example of the ultrasound probe, optionally including one or more of the first and second examples, the ultrasound probe is a linear probe, a sector probe, a convex probe, or an endocavitary probe.

In yet another embodiment, a method for manufacturing an ultrasound transducer structure comprises disposing an acoustic stack on a lens in a cavity of a mold, mixing one or more backing polymer materials, one or more fillers, and one or more additives to obtain a mixture, injecting the mixture into the cavity of the mold such that the mixture contacts a side of the acoustic stack facing away from the lens, solidifying the mixture to form an acoustic backing material bonded to the acoustic stack without adhesives, and separating the ultrasound transducer structure from the mold. In a first example of the method, solidifying the mixture includes one or more of curing the mixture and heating the mixture. In a second example of the method, optionally including the first example, solidifying the mixture is performed at a temperature of 200° C. or less. In a third example of the method, optionally including one or more of the first and second examples, the mixture is a homogeneous distribution of the one or more backing materials, the one or more fillers, and the one or more additives. In a fourth example of the method, optionally including one or more of the first through third examples, the mixture is a uniform density gradient of the one or more backing materials, the one or more fillers, and the one or more additives. In a fifth example of the method, optionally including one or more of the first through fourth examples, the one or more fillers include inorganic particles. In a sixth example of the method, optionally including one or more of the first through fifth examples, the one or more backing polymer materials include one or more or a combination of thermoplastics, thermosetting polymer precursors, and resins. In a seventh example of the method, optionally including one or more of the first through sixth examples, the one or more backing polymer materials include the thermosetting polymer precursors, and solidifying the mixture includes forming a thermosetting polymer from the thermosetting polymer precursors.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound transducer structure, comprising:
a single, continuous lens positioned at a peripheral portion of a housing;
a continuous acoustic stack disposed on the single, continuous lens along a vertical axis; and
an acoustic backing material bonded to a side of the acoustic stack facing away from the lens, along the vertical axis, without any intervening layer between the acoustic backing material and the acoustic stack, such that the acoustic backing material is in face-sharing contact with the side of the acoustic stack,
wherein the acoustic backing material is composed of a solidified blend comprising a backing polymer.

2. The ultrasound transducer structure of claim 1, wherein the backing polymer is formed from one or more or a combination of thermoplastics, thermosetting polymer precursors, and resins.

3. The ultrasound transducer structure of claim 1, wherein no adhesives are disposed on external surfaces or at interfaces of the acoustic backing material and the acoustic stack.

4. The ultrasound transducer structure of claim 1, wherein each of the acoustic backing material, the acoustic stack, and the lens are aligned along the vertical axis within a tolerance of less than 25 µm, the lens being concave.

5. The ultrasound transducer structure of claim 1, wherein the solidified blend further comprises one or more fillers, the one or more fillers including additional polymers, metals, organic materials, or inorganic materials.

6. The ultrasound transducer structure of claim 5, wherein the one or more fillers are in a particulate form.

7. The ultrasound transducer structure of claim 1, wherein the solidified blend further comprises one or more additives including hardeners, crosslinkers, surfactants, polymerization initiators, polymerization accelerators, and stabilizers.

8. The ultrasound transducer structure of claim 1, wherein a bonding between the acoustic stack and the acoustic backing material is stronger than another bonding provided by an adhesive layer between the acoustic stack and the acoustic backing material.

9. An ultrasound probe, comprising:
a housing; and
an ultrasound transducer structure positioned inside the housing, the ultrasound transducer structure comprising:
a single, continuous lens positioned at a peripheral portion of the housing;
a single, continuous acoustic stack conductively coupled to the single, continuous lens along a vertical axis, the acoustic stack comprising an array of piezoelectric elements, where the array of piezoelectric elements comprises piezoceramics, high-dielectric ceramics, or single crystals; and
an acoustic backing material bonded to a side of the acoustic stack facing away from the lens along the vertical axis, the acoustic backing material composed of a solidified blend of a backing polymer matrix, filler particles, and one or more stabilizers,
wherein the ultrasound transducer structure includes no adhesives disposed between the acoustic stack and the acoustic backing material,
the backing polymer matrix is formed from a thermoplastic, thermosetting polymer precursors, or a resin, and
the lens is positioned at the peripheral portion of the housing through which ultrasound radiation is transmitted and received.

10. The ultrasound probe of claim 9, further comprising:
a cable conductively coupled to the ultrasound transducer structure, the cable partially enclosed in the housing,
wherein the ultrasound probe is communicatively coupled to an ultrasound console via the cable.

11. The ultrasound probe of claim 9, wherein the ultrasound probe is communicatively coupled to an ultrasound console via a wireless network.

12. The ultrasound probe of claim 9, wherein the ultrasound probe is a linear probe, a sector probe, a convex probe, or an endocavitary probe.

13. A method for manufacturing an ultrasound transducer structure, comprising:
disposing an acoustic stack on a lens in a cavity of a mold;
mixing one or more backing polymer materials, one or more fillers, and one or more additives to obtain a mixture;
injecting the mixture into the cavity of the mold such that the mixture contacts a side of the acoustic stack facing away from the lens;
solidifying the mixture to form an acoustic backing material bonded to the acoustic stack without adhesives; and
separating the ultrasound transducer structure from the mold, wherein the mixture is a uniform density gradient of the one or more backing polymer materials, the one or more fillers, and the one or more additives.

14. The method of claim 13, wherein solidifying the mixture includes one or more of curing the mixture and heating the mixture.

15. The method of claim 13, wherein solidifying the mixture is performed at a temperature of 200° C. or less.

16. The method of claim 13, wherein the mixture is a homogeneous distribution of the one or more backing polymer materials, the one or more fillers, and the one or more additives.

17. The method of claim 13, wherein the one or more fillers include inorganic particles.

18. The method of claim 13, wherein the one or more backing polymer materials include one or more or a combination of thermoplastics, thermosetting polymer precursors, and resins.

19. The method of claim 18, wherein
the one or more backing polymer materials include the thermosetting polymer precursors, and
solidifying the mixture includes forming a thermosetting polymer from the thermosetting polymer precursors.

* * * * *